United States Patent [19]
Takagawa et al.

[11] Patent Number: 5,495,060
[45] Date of Patent: Feb. 27, 1996

[54] METHOD FOR ISOMERIZING DIMETHYLNAPHTHALENE

[75] Inventors: Makoto Takagawa; Ryusuke Shigematsu; Kazuo Nagagata, all of Tsukuba, Japan

[73] Assignee: Mitsubishi Gas Chemical Company, Inc., Tokyo, Japan

[21] Appl. No.: 214,970

[22] Filed: Mar. 17, 1994

[30] Foreign Application Priority Data

Apr. 1, 1993 [JP] Japan .................. 5-075645

[51] Int. Cl.⁶ .................................. C07C 5/22
[52] U.S. Cl. ........................... 585/481; 585/480
[58] Field of Search .................. 585/477, 478, 585/479, 480, 481

[56] References Cited

U.S. PATENT DOCUMENTS

| | | | |
|---|---|---|---|
| 3,888,938 | 6/1975 | Ogasawara et al. | 585/481 |
| 3,890,403 | 6/1975 | Shimada et al. | 585/478 |
| 4,041,089 | 8/1977 | Allen et al. | 585/481 |
| 4,556,751 | 12/1985 | Maki et al. | 585/481 |
| 4,777,312 | 10/1988 | Bakas et al. | 585/481 |
| 4,783,570 | 11/1988 | Hussmann et al. | 585/481 |

OTHER PUBLICATIONS

Database WPI Week 7550, Derwent Publications Ltd., London, GB; AN 75–82424 of JP–A–50 106 944 (Teijin), Aug. 22, 1975.

Database WPI Week 7515, Derwent Publications Ltd., London, GB; AN 75–25092 of JP–A–50 005 367 (Teijin), Jan. 21, 1975.

Chemical Abstracts, vol. 118, No. 3, Jan. 18, 1993, Columbus, Ohio, US; Abstract No. 22031t, p. 669 of JP–A–4 001 142 (Teijin), Jan. 6, 1992.

Japio (Japan Patent Information Organization) Abstract, p. 97 C 926 for JP 4–1142 (Teijin) (JP 4–1142 was published on Jan. 6, 1992).

*Primary Examiner*—E. Rollins Cross
*Assistant Examiner*—Bekir L. Yildirim
*Attorney, Agent, or Firm*—Frishauf, Holtz, Goodman, Langer & Chick

[57] ABSTRACT

There is disclosed a method for isomerizing dimethylnaphthalene (DMN) in liquid phase under atmospheric pressure by using a catalyst comprising hydrogen-form mordenite which has a molar ratio of silica to alumina ($SiO_2/Al_2O_3$ ratio) of at least 100 and is molded by incorporating alumina as the molding aid therein. According to the above method, the objective 2,6-DMN minimized in the contents of impurities can stably be produced in high selectivity and high yield under mild reaction conditions for a long period of time, while side reactions and deterioration of the catalyst are suppressed to a minimum.

14 Claims, No Drawings

METHOD FOR ISOMERIZING DIMETHYLNAPHTHALENE

BACKGROUND OF THE INVENTION

1. Field of the Invention

The present invention relates to a process for producing 2,6-dimethylnaphthalene which is useful as a starting raw material for 2,6-naphthalene dicarboxylic acid. 2,6naphthalene dicarboxylic acid is industrially important as a starting raw material for polyethylene Naphthalate which is employed for producing high-performance polyester in the form of fiber or film having excellent tensile strength and heat resistance.

2. Description of the Related Art 2,6-dimethylnaphthalene (hereinafter dimethylnaphthalene is sometimes abbreviated to "DMN") is employed as a starting raw material for 2,6-naphthalene dicarboxylic acid and is called upon to have a high purity.

DMN has 10 isomers according to the positions of two methyl groups. It is necessary, however, to produce 2,6-DMN substantially free from an isomer other than 2,6-DMN on a large scale at a low cost. It is well known that in the case of isomerizing DMN, isomerization between adjacent β-positions and isomerization of methyl-migration from one ring to another are unlikely to take place as compared with that between α-position and β-position. Specifically, the above-mentioned 10 DMN isomers are classified into four groups, namely A to D groups as undermentioned with regard to isomerization, and isomerization among different groups is unlikely to take place as compared with that in the same group.

Group A -- 1,5-DMN; 1,6-DMN; and 2,6-DMN

Group B -- 1,8-DMN; 1,7-DMN; and 2,7-DMN

Group C -- 1,4-DMN; 1,3-DMN; and 2,3-DMN

Group D -- 1,2-DMN

As the process for producing 2,6-DMN, there are available a process in which naphthalene or methylnaphthalene is methylated, succeedingly isomerized and separated, isolation process from tar fraction or petroleum fraction and the like. However, the fraction or the reaction product according to any of the above-mentioned processes contains almost all the isomers in the aforesaid four groups, thereby necessitating the isomerization among different groups to take place for the purpose of efficiently producing 2,6-DMN by the isomerization of such isomers. As the method of isomerization among different groups, there is disclosed, for example in Japanese Patent Application Laid-Open No. 88433/1984, a method in which is employed a zeolite having a ten-membered oxygen ring at the inlet of the major cavity. However, the above-disclosed method gives rise to a number of side reactions such as disproportionation in addition to the isomerization because of an elevated temperature required for the reaction, thus lowering the yield of useful 2,6-DMN. That is to say, a process for producing 2,6-DMN by isomerizing a mixture of DMN isomers suffers from the disadvantage that a number of DMN isomers contained that are unlikely to be converted to 2,6-DMN because of their belonging to the group other than the group of 2,6-DMN lower the yield of 2,6-DMN, necessitate steps of separation from mixed isomers and thereby make the process inefficient as an industrial process for the production of 2,6-DMN.

On the other hand, Japanese Patent Application Laid-Open Nos. 134634/1974, 89353/1975 and 76852/1973 disclose a process for producing o-tolylpentene-2 in high yield from o-xylene and butadiene; a process for producing 1,5-dimethyltetralin by cyclizing o-tolylpentene-2; and a process for producing 1,5-DMN in high yield and in high selectivity by dehydrogenating 1,5-dimethyltetralin, respectively. In the case where 1,5-DMN thus obtained is used as the starting material for the production of 2,6-DMN, it is advantageous in that 2,6-DMN can be produced without difficult isomerization among different isomer groups, since both 1,5-DMN and 2,6-DMN belong the same group with regard to isomerization.

There are proposed a number of processes for producing 2,6-DMN by isomerizing 1,5-DMN, for example, Japanese Patent Publication No. 50622/1972 discloses a method of isomerization in the gaseous phase by the use of a silica-alumina catalyst, Japanese Patent Publication No. 4008/1983 discloses a method of isomerization in liquid phase by the use of mordenite containing chromium or the like as a catalyst, and U.S. Pat. No. 4962260 discloses a method of isomerization by the use of β-zeolite or Y-type zeolite.

Nevertheless, the method in Japanese Patent Publication No. 50622/1972, although high in terms of the concentration of 2,6-DMN contained in the reaction liquid, has deficiencies in that considerable amounts of 2,7-DMN and 1,7-DMN are produced which are different in isomerization group from 2,6-DMN and further, considerable amounts of monomethylnaphthalene and trimethylnaphthalene are produced by disproportionation. The method in Japanese Patent Publication No. 4008/1983, although low in the production of 2,7-DMN and in side reactions such as disproportionation, suffers the defect that the efficiency of isomerization into 2,6-DMN is limited. In addition, the method in U.S. Pat. No. 4962260, although low in the side reaction such as disproportionation, suffers the disadvantages that the production of isomers belonging to different isomerization groups such as 2,7-DMN group are high and further the efficiency of isomerization into 2,6-DMN is insufficient.

That is to say, it is the present situation that any of the prior art processes can not attain a high efficiency of isomerization into the objective 2,6-DMN, while suppressing the isomerization into a group different from 2,6-DMN group as well as the side reaction such as disproportionation.

The production of 2,7-DMN not only decreases the yield of the objective 2,6-DMN in the isomerization step, but also brings about the loss of 2,6-DMN and lowers the purity thereof in the step of crystallization/separation after the isomerization step because of the formation of the binary eutectic-mixture of 2,7- and 2,6-isomers and the ternary eutectic-mixture of 2,7-, 2,6- and 1,5-isomers. Moreover, the side reaction such as disproportionation leads to a decrease in the yield of 2,6-DMN.

It is well known that various solid acids are useful as the catalyst for the isomerization of an aromatic hydrocarbon. Mordenite is one of solid acids and is frequently used for isomerizing DMN. In addition to the above-mentioned Japanese Patent Publication No. 4008/1983, Japanese Patent Publication No. 11690/1981 discloses a method in which H-type mordenite is employed as the principal catalyst along with bentonite or acid clay as the cocatalyst and Japanese Patent Publication No. 49054/1980 discloses a method in which is used a mordenite having a molar ratio of silica to alumina of 10 to 50.

However, even with the above-disclosed methods, the isomerization into DMN belonging to a different group such as 2,7-DMN group, the side reaction such as disproportionation or the like take place, thus failing to achieve a high efficiency of isomerization into 2,6-DMN.

Under such circumstances, intensive research and investigation were made by the present inventors in order to develop a process for producing 2,6-DMN by isomerizing 1,5-DMN which process is capable of realizing a high efficiency of isomerization from 1,5-DMN to 2,6-DMN, suppressing the formation of DMN belonging to a different group such as 2,7-DMN group as well as the side reaction such as disproportionation, and at the same time, imparting a prolonged service life to the catalyst. As a result, it has been found by the present inventors that it is possible to realize a high efficiency of isomerization into the objective 2,6-DMN, suppress the formation of DMN belonging to a different group such as 2,7-DMN group and the side reaction such as disproportionation and maintain favorable performance over a long period of time by effecting isomerization at a reaction temperature of 270° C. or lower in liquid phase by the use of a catalyst comprising mordenite being substantially of hydrogen form having a molar ratio of silica to alumina (hereinafter referred to as "$SiO_2/Al_2O_3$ ratio") of 100 or higher. The present invention has been accomplished on the basis of the above-mentioned finding.

SUMMARY OF THE INVENTION

The present invention provides a method for isomerizing DMN which comprises isomerizing DMN in liquid phase by the use of a catalyst comprising mordenite which is substantially of hydrogen form having a $SiO_2/Al_2O_3$ ratio of 100 or higher and is molded by incorporating alumina as a molding aid therein.

DESCRIPTION OF PREFERRED EMBODIMENT

There is employed in the present invention, hydrogen form (H-form) mordenite as a catalyst, in which utmost importance should be attached to the $SiO_2/Al_2O_3$ ratio. The ratio should be at least 100, preferably at least 150, more preferably at least 200.

Although the use of mordenite as a catalyst enables DMN to be isomerized as mentioned hereinbefore, a conventional mordenite is low in activity because of its $SiO_2/Al_2O_3$ ratio being only about 30 and thus necessitates an elevated temperature as high as 300° C. for the purpose of isomerizing DMN, resulting in inevitable occurrence of serious side reaction such as disproportionation and the formation of DMN belonging to a different group. The aforestated fact is clear from the working examples in the foregoing patent gazettes.

As is the case with other zeolite, mordenite can be enhanced in its $SiO_2/Al_2O_3$ ratio to some extent by treating it with a mineral acid such as hydrochloric acid, but it is difficult to enhance the ratio to 50 or more under an ordinary treatment conditions. In the case where the ratio more than 50 is desired, the treatment conditions must be made more severe, whereby the mordenite structure is inevitably destroyed.

A method of greatly enhancing a $SiO_2/Al_2O_3$ ratio in mordenite has hitherto been unavailable, forcing mordenite having a relatively low $SiO_2/Al_2O_3$ ratio to be employed as a catalyst, and therefore sufficient catalytic activity of mordenite can not be obtained. Attempts have been made to improve the catalytic activity and selectivity of mordenite by incorporating a variety of metals or cocatalysts therein, but the purpose of embodying a high isomerization efficiency in the same group and suppressing the formation of DMN belonging to a different group and the side reaction such as disproportionation has not sufficiently been accomplished. That is to say, the formation of DMN belonging to a different group and the occurrence of the side reaction such as disproportionation are accelerated with increasing efficiency of isomerization into 2,6-DMN and consequently, the efficiency of isomerization can not be enhanced for the purpose of restricting the formation of such undesirable DMN and the side reaction to low levels.

With regard to $SiO_2/Al_2O_3$ ratio in mordenite, Japanese Patent Publication No. 49054/1980 discloses a method of isomerizing DMN in gaseous phase by the use of H-form mordenite with a $SiO_2O_3$ ratio of 10 or more as a catalyst. According to the working examples in the disclosure, in the case of increasing the ratio stepwise from 10 to 15, 25 and 97, efficiency of isomerization into 2,6-DMN increases and the formation of 2,7-DMN decreases with an increase in the ratio in the range of 10 to 25, but isomerization efficiency decreases and the 2,7-DMN formation increases with an increase in the ratio up to 97, which indicates that there lies an optimum value of $SiO_2/Al_2O_3$ ratio. However, the performance result therein reveals that even with a $SiO_2/Al_2O_3$ ratio regarded as being optimum, an elevated temperature of 350° C. or higher is required and the concentration of 2,6-DMN in the reaction liquid is not sufficient.

As a result of intensive research made by the present inventors on the isomerization reaction of DMN by using mordenite, it has been found that the application of H-form mordenite having a $SiO_2/Al_2O_3$ ratio of 100 or more, preferably 150 or more, more preferably 200 or more to the reaction as the catalyst can attain a high efficiency of isomerization into the objective 2,6-DMN and at the same time, suppress almost perfectly the isomerization into DMN belonging to a different group and the occurrence of side reaction such as disproportionation, at a reaction temperature lower than that in the prior arts.

As the zeolite whose $SiO_2/Al_2O_3$ ratio can be enhanced, mention may be made of Y-type zeolite and ZSM5, which however, are not suited for the purpose of the present invention which consists in the realization of high isomerization efficiency in the same group and in the suppression of the formation of DMN belonging to a different group as well as the occurrence of the side reaction such as disproportionation. As disclosed in the aforesaid U.S. Pat. No. 4962260, by using Y-type zeolites it is difficult to suppress the formation of DMN belonging to a different group and the occurrence of the side reaction such as disproportionation. The use of Y-type zeolite with a high $SiO_2/Al_2O_3$ ratio of 100 or more, which ratio exhibits an excellent effect in the mordenite in the present invention, resulted in failure to achieve favorable results as shown later in the comparative example. Likewise as disclosed in Japanese Patent Application Laid-Open No. 69043/1985, a zeolite comprising ten-membered oxygen ring which is typified by ZSM5 is used for isomerizing DMN between different groups and therefore is not suitable for the present invention.

As mordenite, mention may be made of the Na-form, the Ca-form and the like, but the present invention is characterized by the use of mordenite consisting essentially of H-form mordenite. Mordenite containing an alkali metal and/or an alkaline earth metal is not suited to the reaction of the present invention because of its low catalytic-activity.

For the aforesaid reason, mordenite of the Na-form, the Ca-form or the like needs to be converted to mordenite of the H-form. As a method for converting mordenite of the Na-form, the Ca-form or the like to mordenite of the H-form, there are well known a method in which mordenite of the above form is converted to that of $NH_4$-form, followed by removing $NH_3$ through heating and a method in which mordenite of the above form is treated with a mineral acid such as hydrochloric acid. Of the aforesaid methods, the latter method is preferable. The aforementioned splendid effect of the mordenite converted to H-form increases with a decrease in the contents of an alkali metal and/or an alkaline earth metal contained in the mordenite. The content of such metal(s) is usually 1% or less, preferably 0.5% or less, more preferably 0.1% or less each by weight.

The mordenite of the H-form having a $SiO_2/Al_2O_3$ ratio of 100 or higher has an extremely high selectivity and scarcely causes side reaction such as disproportionation in the course of isomerization. In Japanese Patent Publication No. 4008/1983 and Japanese Patent Application Laid Open No. 117756/1975, the concentrations of monomethylnaphthalene and/or trimethylnaphthalene in DMN as the starting material are restricted to at most 20% by weight. The reason for this is that the disproportionation activity of the catalyst used therein is high and consequently, the disproportionation of monomethylnaphthalene and/or trimethylnaphthalene is caused when they are contained in the starting material in a high concentration, thereby forming DMN belonging to a different group. As opposed to the foregoing, the catalyst to be used in the present invention has an extremely low disproportionation-activity, and does not specifically limit the concentrations of monomethylnaphthalene and/or trimethylnaphthalene in DMN as the starting material. This is also one of the significant advantages of the present invention. However, in the case of monomethylnaphthalene and/or trimethylnaphthalene are contained in high concentration in the starting material for the present invention, it is necessary to enlarge a reactor in proportion to the concentration and hence, the allowable concentrations of impurities other than DMN in the starting material are determined from the viewpoint of economical efficiency of the process.

The isomerization reaction is carried out in the liquid phase in the present invention. It is possible, however, to proceed with the reaction in the gaseous phase by the use of a solvent such as benzene. The gaseous phase reaction can proceed with the reaction at a temperature lower than that in the liquid-phase reaction and can almost completely suppress the isomerization into a different group as well as the occurrence of the side reaction such as disproportionation.

Nevertheless in the case of isomerization reaction in the gaseous phase, catalytic activity is remarkably lowered with the progress of the reaction and long-term continuous operation is made difficult. On the contrary, it has been found that in the case of isomerization reaction in liquid phase, lowering of catalytic activity is suppressed and long-term stable performance result is obtainable.

Since the H-form mordenite having a $SiO_2/Al_2O_3$ ratio of 100 or more used in the present invention is highly active, the reaction proceeds satisfactorily even at a temperature of 270° C. or lower.

The boiling point of DMN varies depending on the type of isomer but ranges from 260° to 270° C. and accordingly, the reaction can be carried out at atmospheric pressure unless a low boiling solvent is used therein. On the other hand in Japanese Patent Publication No. 4008/1983 and Japanese Patent Application Laid-Open Nos. 108246/1975 and 117756/1975, catalysts comprising mordenite having a $SiO_2/Al_2O_3$ ratio in the range of 10 to 95 which is impregnated with various metals are used for isomerizing DMN in liquid phase, but the low activity of the catalysts necessitates a high reaction temperature and obliges the reaction system to be pressurized.

The reaction process applicable to the isomerization reaction according to the present invention is not specifically limited, but is exemplified by any of the batch-wise system and the flow system, of which the flow system is preferable from an industrial standpoint. As the flow system, any of fixed bed, moving bed and fluidized bed is applicable to the system and among them the fixed-bed flow system is prevailing. In the case of the fixed-bed flow system being applied to the system, molded mordenite is used therein. As a molding aid for mordenite, there are used alumina, silica and clay such as bentonite, among which alumina is suitable. A clay such as bentonite contains a variety of metals, which is the cause for deteriorating the isomerization activity. Silica is not practical as a molding aid, since it shortens the service life of the catalyst.

Alumina as the molding aid, when used in an appropriate amount, exhibits a favorable result from the aspect of service life of the catalyst without lowering the isomerization activity. An unreasonably small amount thereof to be used results in failure to attain sufficient strength of the molded catalyst, whereas an excessively large amount thereof exerts an evil influence on the service life of the catalyst though the problem with strength is solved. The amount of alumina to be used therefor is preferably 5 to 50 parts by weight, particularly preferably 10 to 30 parts by weight based on 100 parts by weight of the mordenite.

In the method according to the present invention, a solvent is not required in particular but can be used in connection with the subsequent purification step as described hereunder. As a method for separating the objective DMN from the isomerization reaction liquid, any of crystallization and adsorption is applicable thereto. The use of an appropriate solvent in the purification step is sometimes advantageous. In this case, the solvent to be used in the above-mentioned purification step can also be used for the isomerization reaction according to the present invention. Depending upon the type of solvent, however, the reaction system needs to be pressurized in order to proceed with the reaction in liquid phase. The decision as to whether an solvent is to be used or not in the isomerization step should be made taking into consideration the overall economical efficiency in combination with the succeeding purification step.

The isomerization reaction according to the method of the present invention is put into practice at a temperature in the range of 200° to 270° C., preferably 230° to 260° C. A reaction temperature higher than the aforesaid upper limit leads to likelihood of isomerization into a different group and occurrence of the side reaction such as disproportionation, whereas that lower than the above lower limit is uneconomical because of a lowered rate of isomerization. In the case where the isomerization reaction according to the method of the present invention is carried out at a temperature in the range of 200° to 270° C., the objective 2,6-DMN is obtained in the reaction liquid in a concentration of 47 to 50% by weight based on the total DMN belonging to 2,6-DMN group, being hardly accompanied by the formation of the isomer belonging to a different group such as 2,7-DMN group or the occurrence of the side reaction such as disproportionation.

In the case of carrying out the present invention by means of a flow system, the weight hourly space velocity (WHSV) is 0.05~5 $h^{-1}$, preferably 0.1 to 2 $h^{-1}$, more preferably 0.2 to 1 $h^{-1}$. At a lower WHSV, the isomerization reaction proceeds at a lower reaction temperature, but a reactor needs to be enlarged, thus making the process uneconomical. On the other hand at a higher WHSV, the reaction temperature is required to be raised to attain a desired isomerization efficiency, causing the likelihood of isomerization to a different group and occurrence of disproportionation and further the reaction system needs to be pressurized to proceed with the reaction in liquid phase, whereby the process is made uneconomical.

In a batch-wise process, the amount of the catalyst to be used is 0.1 to 10 parts, preferably 0.3 to 5 parts by weight based on 100 parts by weight of starting material, and the reaction time varies depending on the ratio of the catalyst to the starting material and reaction temperature, and usually ranges from 10 minutes to 2 hours.

As described hereinbefore, the method for isomerizing DMN according to the present invention is capable of suppressing the isomerization into a different group of isomer such as 2,7-DMN as well as the occurrence of the side reaction such as disproportionation and of achieving a high efficiency of isomerization into the objective 2,6-DMN, thus rendering itself highly significant from the industrial viewpoint.

The method according to the present invention will be described in detail with reference to the following examples and comparative examples, which examples shall not be construed to limit the present invention thereto.

EXAMPLES 1 AND 2

H-form mordenite having a $SiO_2/Al_2O_3$ ratio of 203 (produced by Tosoh Corporation) in an amount of 100 g and 20 g of alumina sol (alumina content of 70% by weight, produced by Catalysts & Chemicals Industries Co., Ltd.) were placed in a stainless steel-made vessel, incorporated with demineralized water and sufficiently kneaded with each other. The kneaded product was dried at 110° C., calcined at 500° C. in the air for 2 hours and crushed to collect the crushed product of 1.0 to 2.0 mm in particle diameter as the catalyst.

Then, 5 g of the catalyst was packed in a stainless steel-made tubular reactor with 13 mm inside diameter, which was sufficiently purged with nitrogen and thereafter heated to a prescribed temperature in an atmosphere of nitrogen and maintained at the temperature. DMN as the starting material was fed in the aforesaid reactor from the lower part thereof to proceed with the isomerization reaction under atmospheric pressure. The resultant reaction liquid was taken out from the upper part thereof, and analyzed to determine the composition thereof by gas chromatography and evaluate the performance results of isomerization reaction. Table 1 gives the composition of the starting material used, reaction conditions and performance results, for each of the examples. The reaction temperature was raised from 250° C. to 260° C. in Example 1,-from 240° C. to 255° C. in Example 2 after the elapse of time from the start of reaction of 1500 hours in Example 1, 2400 hours in Example 2.

EXAMPLES 3 AND 4

H-form mordenite having a $SiO_2/Al_2O_3$ ratio of 16 (produced by Tosoh Corporation) was treated with 3N hydrochloric acid into H-form mordenite having $SiO_2/Al_2O_3$ ratios of 113 in Example 3 and 154 in Example 4. By the use of each mordenite, a catalyst in the form of a molding was prepared and employed for the isomerization reaction in the same manner as in Example 1. The results are given in Tables 1 & 2.

EXAMPLE 5

The procedure in Example 1 was repeated to prepare a molded catalyst and the isomerization reaction was carried out in the same manner as in Example 1 except that 40 g of the alumina sol was used. The results are given in Table 2.

COMPARATIVE EXAMPLES 1 AND 2

The procedure in Example 1 was repeated to prepare catalysts except that H-form mordenite having a $SiO_2/Al_2O_3$ ratio of 16 (produced by Tosoh Corporation) was used in Comparative Example 1 and H-form mordenite having a $SiO_2/Al_2O_3$ ratio of 33 (produced by Catalysts & Chemicals Industries Co., Ltd.) was used in Comparative Example 2 in place of the H-form mordenite having a $SiO_2/Al_2O_3$ ratio of 203. Subsequently the procedure in Example 2 was repeated to carry out the isomerization reaction except that the reaction temperatures were varied and that the reaction systems were pressurized to maintain high temperature systems in liquid phases. Table 3 gives the reaction conditions and performance results. As can be seen from Table 3, high temperatures were required in order to enhance 2,6-DMN concentration in the reaction product, whereby the reaction system needed to be pressurized and further, the reaction was accompanied by remarkable formation of 2,7- and 1,7-DMN and conspicuous side reaction such as disproportionation.

COMPARATIVE EXAMPLE 3

The procedure in Example 1 was repeated to prepare a catalyst except that H-form ultra-stabilized Y-type zeolite having a $SiO_2/Al_2O_3$ ratio of 206 (USY, produced by Tosoh Corporation) was used in place of the H-form mordenite having a $SiO_2/Al_2O_3$ ratio of 203. Subsequently the isomerization reaction was carried out according to the procedure in Comparative Example 1. Table 3 gives the reaction conditions and performance results. As can be seen from Table 3, high temperature was required in order to enhance 2,6-DMN concentration in the reaction product, whereby the reaction system needed to be pressurized and further, the reaction was accompanied by remarkable formation of 2,7- and 1,7-DMN and conspicuous side reaction such as disproportionation.

COMPARATIVE EXAMPLE 4

The procedure in Example 2 was repeated to prepare the catalyst and carry out the isomerization reaction except that 20% by weight solution of the starting material in benzene was subjected to isomerization reaction in gaseous phase at reaction temperatures different from those in Example 2. Table 4 gives the reaction conditions and performance results. It has been proved from the above results that although the reaction sufficiently proceeds at a temperature lower than that in Example 2, the catalytic activity is greatly deteriorated.

COMPARATIVE EXAMPLE 5

The procedure in Example 1 was repeated to prepare the catalyst and carry out the isomerization reaction except that 70 g of silica sol (silica content of 20% by weight, produced by Catalysts & Chemicals Industries Co., Ltd.) was employed in place of 20 g of alumina sol (alumina content of 70% by weight, produced by Catalysts & Chemicals Industries Co., Ltd.). Table 4 gives the reaction conditions and performance results.

The reaction temperature was raised after 1500 hours from the start of reaction in Example 1 and after 970 hours therefrom in this comparative example. As can be seen from Tables 1 & 4, the performance results after a lapse of time of 1022 hours in this comparative example are inferior to those after 2840 hours in Example 1, thereby proving that the use of silica as a binder, that is, a molding aid remarkably deteriorates the catalytic activity.

TABLE 1

|  | Example 1 | | Example 2 | | Example 3 |
| --- | --- | --- | --- | --- | --- |
| Starting material (wt %) | | | | | |
| 1,5-DMN | 12.43 | | 99.83 | | 9.33 |
| 1,6-DMN | 78.32 | | 0 | | 57.01 |
| 2,6-DMN | 8.35 | | 0 | | 6.15 |
| Other DMN | 0.33 | | 0.07 | | 0.24 |
| Low boiling substance | 0.18 | | 0.10 | | 0.44 |
| MMN*[1] | 0.23 | | 0 | | 13.87 |
| TMN*[2] | 0.14 | | 0 | | 12.59 |
| High boiling substance | 0.02 | | 0 | | 0.37 |
| Reaction conditions | | | | | |
| temperature (°C.) | 250 | 260 | 240 | 255 | 240 |
| WHSV (h$^{-1}$)*[3] | 1 | 1 | 0.5 | 0.5 | 0.5 |
| reaction time (h)*[4] | 20 | 2840 | 31 | 3290 | 25 |
| Reaction liquid (wt %) | | | | | |
| 1,5-DMN | 7.29 | 10.04 | 7.41 | 9.83 | 5.75 |
| 1,6-DMN | 43.09 | 41.55 | 43.69 | 42.81 | 31.68 |
| 2,6-DMN | 48.50 | 47.49 | 48.58 | 47.20 | 34.76 |
| Other DMN | 0.36 | 0.33 | 0.11 | 0.06 | 0.29 |
| Low boiling substance | 0.16 | 0.18 | 0.10 | 0.10 | 0.46 |
| MMN*[1] | 0.26 | 0.23 | 0.07 | 0 | 14.02 |
| TMN*[2] | 0.22 | 0.16 | 0.04 | 0 | 12.63 |
| High boiling substance | 0.12 | 0.02 | 0 | 0 | 0.41 |
| 2,6-DMN in 2,6-group | 49.05 | 47.93 | 48.74 | 47.28 | 48.15 |

*[1]Monomethylnaphthalene
*[2]Trimethylnaphthalene
*[3]WHSV = g-starting material/g-catalyst · h
*[4]Time elapsed from start of reaction

TABLE 2

|  | Example 4 | | Example 5 | |
| --- | --- | --- | --- | --- |
| Starting material (wt %) | | | | |
| 1,5-DMN | 12.43 | | 12.43 | |
| 1,6-DMN | 78.32 | | 78.32 | |
| 2,6-DMN | 8.35 | | 8.35 | |
| Other DMN | 0.33 | | 0.33 | |
| Low boiling substance | 0.18 | | 0.18 | |
| MMN*[1] | 0.23 | | 0.23 | |
| TMN*[2] | 0.14 | | 0.14 | |
| High boiling substance | 0.02 | | 0.02 | |
| Reaction conditions | | | | |
| temperature (°C.) | 250 | 260 | 250 | 260 |
| WHSV (h$^{-1}$)*[3] | 1 | 1 | 1 | 1 |
| reaction time (h)*[4] | 18 | 2420 | 23 | 2632 |
| Reaction liquid (wt %) | | | | |
| 1,5-DMN | 7.51 | 10.16 | 7.23 | 9.72 |
| 1,6-DMN | 43.12 | 41.73 | 43.36 | 42.19 |
| 2,6-DMN | 48.13 | 47.14 | 48.21 | 47.17 |
| Other DMN | 0.40 | 0.34 | 0.37 | 0.33 |
| Low boiling substance | 0.19 | 0.18 | 0.19 | 0.18 |
| MMN*[1] | 0.26 | 0.24 | 0.26 | 0.23 |
| TMN*[2] | 0.21 | 0.17 | 0.23 | 0.16 |
| High boiling substance | 0.18 | 0.04 | 0.15 | 0.02 |
| 2,6-DMN in 2,6-group | 48.73 | 47.60 | 48.80 | 47.61 |

*[1]Monomethylnaphthalene
*[2]Trimethylnaphthalene
*[3]WHSV = g-starting material/g-catalyst · h
*[4]Time elapsed from start of reaction

TABLE 3

|  | Comparative Example 1 | | Comparative Example 2 | | Comparative Example 3 | |
| --- | --- | --- | --- | --- | --- | --- |
| Starting material (wt %) | | | | | | |
| 1,5-DMN | 12.43 | | 12.43 | | 12.43 | |
| 1,6-DMN | 78.32 | | 78.32 | | 78.32 | |
| 2,6-DMN | 8.35 | | 8.35 | | 8.35 | |
| Other DMN | 0.33 | | 0.33 | | 0.33 | |
| Low boiling substance | 0.18 | | 0.18 | | 0.18 | |
| MMN*[1] | 0.23 | | 0.23 | | 0.23 | |
| TMN*[2] | 0.14 | | 0.14 | | 0.14 | |
| High boiling substance | 0.02 | | 0.02 | | 0.02 | |
| Reaction conditions | | | | | | |
| pressure (atm) | 1 | 5 | 1 | 5 | 1 | 5 |
| temperature (°C.) | 260 | 290 | 260 | 290 | 260 | 290 |
| WHSV (h$^{-1}$)*[3] | 1 | 1 | 1 | 1 | 1 | 1 |
| reaction time (h)*[4] | 14 | 40 | 18 | 38 | 12 | 31 |
| Reaction liquid (wt %) | | | | | | |
| 1,5-DMN | 25.73 | 7.88 | 22.67 | 7.99 | 30.90 | 9.48 |
| 1,6-DMN | 40.69 | 41.80 | 38.79 | 40.16 | 35.72 | 41.70 |
| 2,6-DMN | 32.68 | 44.58 | 37.64 | 43.35 | 32.48 | 43.60 |
| Other DMN | 0.33 | 1.77 | 0.33 | 3.01 | 0.33 | 1.05 |
| Low boiling substance | 0.18 | 0.49 | 0.18 | 0.73 | 0.18 | 0.88 |
| MMN*[1] | 0.23 | 1.42 | 0.23 | 1.86 | 0.23 | 0.86 |
| TMN*[2] | 0.14 | 1.07 | 0.14 | 1.53 | 0.14 | 1.03 |
| High boiling substance | 0.02 | 0.99 | 0.02 | 1.37 | 0.02 | 1.40 |
| 2,6-DMN in 2,6-group | 32.98 | 47.29 | 37.98 | 47.38 | 32.77 | 46.00 |

*[1]Monomethylnaphthalene
*[2]Trimethylnaphthalene
*[3]WHSV = g-starting material/g-catalyst · h
*[4]Time elapsed from start of reaction

TABLE 4

|  | Comparative Example 4 | | | Comparative Example 5 | | |
| --- | --- | --- | --- | --- | --- | --- |
| Starting material (wt %) | | | | | | |
| 1,5-DMN | 99.83 | | | 12.43 | | |
| 1,6-DMN | 0 | | | 78.32 | | |
| 2,6-DMN | 0 | | | 8.35 | | |
| Other DMN | 0.07 | | | 0.33 | | |
| Low boiling substance | 0.10 | | | 0.18 | | |
| MMN*[1] | 0 | | | 0.23 | | |
| TMN*[2] | 0 | | | 0.14 | | |
| High boiling substance | 0 | | | 0.02 | | |
| Reaction conditions | | | | | | |
| temperature (°C.) | 150 | 150 | 240 | 260 | 250 | 260 |
| WHSV (h$^{-1}$)*[3] | 1 | 1 | 1 | 1 | 1 | 1 |
| reaction time (h)*[4] | 12 | 106 | 308 | 342 | 20 | 1022 |
| Reaction liquid (wt %) | | | | | | |
| 1,5-DMN | 6.00 | 16.61 | 12.08 | 8.85 | 6.97 | 14.54 |
| 1,6-DMN | 40.82 | 37.48 | 43.81 | 43.23 | 44.49 | 40.72 |
| 2,6-DMN | 52.94 | 45.74 | 43.94 | 46.18 | 47.43 | 43.82 |
| Other DMN | 0.10 | 0.07 | 0.07 | 0.21 | 0.38 | 0.33 |
| Low boiling substance | 0.10 | 0.10 | 0.10 | 0.41 | 0.20 | 0.18 |
| MMN*[1] | 0.02 | 0 | 0 | 0.31 | 0.24 | 0.23 |
| TMN*[2] | 0.02 | 0 | 0 | 0.24 | 0.18 | 0.16 |
| High boiling substance | 0 | 0 | 0 | 0.57 | 0.11 | 0.02 |
| 2,6-DMN in 2,6-group | 53.07 | 45.82 | 44.01 | 47.00 | 47.96 | 44.23 |

*[1]Monomethylnaphthalene
*[2]Trimethylnaphthalene
*[3]WHSV = g-starting material/g-catalyst · h
*[4]Time elapsed from start of reaction
*[5]Solution of starting material in benzene with concentration of 20% by weight

What is claimed is:

1. A method of isomerizing dimethylnaphthalene which comprises isomerizing dimethylnaphthalene at a temperature of no more than 270° C. in a liquid phase in the presence of a molded catalyst composition which consists essentially of (i) mordenite which is substantially in a hydrogen form, said mordenite having a molar ratio of silica to alumina of at least 150, said mordenite having a total content of alkali metals and alkaline earth metals of no more than 1% by weight, expressed in terms of each of the alkali metals and alkaline earth metals, and (ii) alumina as a molding aid.

2. The method according to claim 1 wherein the alumina is contained in an amount of 5 to 50 parts by weight based on 100 parts by weight of the mordenite.

3. The method according to claim 1 wherein the total content of alkali metals and alkaline earth metals contained in the mordenite is at most 0.5% by weight expressed in terms of each of the metals.

4. The method according to claim 1 wherein the temperature is 200° to 270° C.

5. The method according to claim 1 wherein the isomerization reaction is effected by a fixed-bed flow system under atmospheric pressure.

6. The method according to claim 1, wherein the silica to alumina ratio is at least 200.

7. The method according to claim 6, wherein the total amount of alkali metals and alkaline earth metals in the mordenite is 0.5 weight % or less.

8. The method according to claim 6, wherein the total amount of alkali metals and alkaline earth metals in the mordenite is 0.1 weight % or less.

9. The method according to claim 7, wherein the alumina is contained in an amount of 10 to 30 parts by weight based on 100 parts by weight of the mordenite.

10. The method according to claim 9, wherein the temperature is 230° to 260° C.

11. The method according to claim 10, wherein the isomerized dimethylnaphtalene comprises 2,6-dimethylnaphtalene.

12. The method according to claim 5, wherein the isomerization is carried out at a weight hourly space velocity of 0.05 to 5 hours$^{-1}$.

13. The method according to claim 5, wherein the isomerization is carried out at a weight hourly space velocity of 0.1 to 2 hours$^{-1}$.

14. The method according to claim 5, wherein the isomerization is carried out at a weight hourly space velocity of 0.2 to 1 hour$^{-1}$.

* * * * *